(12) United States Patent
Han et al.

(10) Patent No.: US 6,518,216 B1
(45) Date of Patent: Feb. 11, 2003

(54) CATALYST USEFUL FOR OXIDATION OF ALKANES

(75) Inventors: Scott Han, Lawrenceville, NJ (US); Dominique Hung Nhu Le, Upper Darby, PA (US); Nneka Namono McNeal, Ambler, PA (US)

(73) Assignee: Rohm and Haas Company, Philadelphia, PA (US)

( * ) Notice: Subject to any disclaimer, the term of this patent is extended or adjusted under 35 U.S.C. 154(b) by 122 days.

(21) Appl. No.: 09/659,289

(22) Filed: Sep. 12, 2000

Related U.S. Application Data

(60) Provisional application No. 60/154,160, filed on Sep. 15, 1999.

(51) Int. Cl.[7] .............................. B01J 23/22; B01J 23/28
(52) U.S. Cl. ................. 502/215; 502/300; 502/304; 502/305; 502/308; 502/309; 502/311; 502/312; 502/313; 502/315; 502/319; 502/321; 502/324; 502/337; 502/339; 502/349; 502/350; 502/353; 502/355
(58) Field of Search ...................... 502/300, 304, 502/305, 308, 309, 311, 312, 313, 315, 316, 319, 321, 324, 337, 338, 339, 349, 350, 353, 355, 217, 64, 215

(56) References Cited

U.S. PATENT DOCUMENTS

| | | | |
|---|---|---|---|
| 4,233,139 A | * | 11/1980 | Murrell et al. .............. 208/112 |
| 4,524,236 A | | 6/1985 | McCain |
| 4,552,860 A | * | 11/1985 | Murib ......................... 502/242 |
| 4,892,856 A | * | 1/1990 | Kawajiri et al. ............. 502/247 |
| 4,925,980 A | * | 5/1990 | Matsumoto et al. ......... 502/209 |
| 4,954,650 A | * | 9/1990 | Abe et al. .................... 422/188 |
| 5,049,692 A | * | 9/1991 | Hatano et al. ............... 558/318 |
| 5,380,933 A | | 1/1995 | Ushikubo et al. |
| 5,700,752 A | * | 12/1997 | Kurimoto et al. ........... 502/305 |
| 5,705,685 A | | 1/1998 | Lyons et al. |
| 5,990,248 A | | 11/1999 | Lyons et al. |
| 6,166,241 A | * | 12/2000 | Kayou et al. ................ 558/318 |
| 6,166,263 A | * | 12/2000 | Etzkorn et al. .......... 568/469.9 |

FOREIGN PATENT DOCUMENTS

| | | |
|---|---|---|
| DE | 198 47 656 A1 | 5/1999 |
| EP | 0 032 012 A2 | 7/1981 |
| EP | 0 281 280 A1 | 9/1988 |
| EP | 0 529 853 A2 | 3/1993 |
| EP | 0 603 836 A1 | 6/1994 |
| EP | 0 658 259 * | 12/1995 |
| EP | 0 685 259 * | 12/1995 |
| EP | 0 970 942 A1 | 1/2000 |
| JP | 7-53448 * | 2/1995 |

* cited by examiner

Primary Examiner—Stanley S. Silverman
Assistant Examiner—Christina Ildebrando
(74) Attorney, Agent, or Firm—Alan Holler

(57) ABSTRACT

A catalyst useful for the gas phase oxidation of alkanes to unsaturated aldehydes or carboxylic acids is disclosed. Processes for preparing the catalyst and using the catalyst to convert alkanes to unsaturated aldehydes or carboxylic acids are also disclosed.

9 Claims, No Drawings

CATALYST USEFUL FOR OXIDATION OF ALKANES

CROSS REFERENCE TO RELATED APPLICATIONS

This patent application claims the benefit of the earlier filing date of the prior filed co-pending Provisional application serial No. 60,154,160 filed on Sep. 15, 1999 under 37 CFR 1.78(a)(4).

This invention relates to catalysts useful in the preparation of unsaturated aldehydes and acids. In particular, the invention relates to a catalyst which is efficient in converting alkanes to unsaturated aldehydes and carboxylic acids and a process for preparing unsaturated aldehydes and carboxylic acids using the catalyst.

Unsaturated aldehydes and carboxylic acids are important commercial chemicals. Of particular importance is (meth)acrylic acid. The highly reactive double bond and acid function of (meth)acrylic acid makes it especially suitable as a monomer which may be polymerized alone or with other monomers to produce commercially important polymers. These unsaturated acids are also useful as a starting material for esterification to produce commercially important (meth)acrylate esters. Materials derived from (meth)acrylic acid or esters of (meth)acrylic acids are useful as plastic sheets and parts, paints and other coatings, adhesives, caulks, sealants, and detergents as well as other applications.

The production of unsaturated carboxylic acids by oxidation of an olefin is well known in the art. Acrylic acid, for instance, may be commercially manufactured by the gas phase oxidation of propylene. It is also known that unsaturated carboxylic acids may also be prepared by oxidation of alkanes. For instance, acrylic acid may be prepared by the oxidation of propane. Such a process is especially desirable because alkanes generally have a lower cost than olefins. A suitable catalyst and process for the oxidation of alkanes to unsaturated aldehydes or carboxylic acids, which are commercially viable, is a continuous goal of (meth)acrylic acid manufactures and has yet to be achieved.

One impediment for the production of a commercially viable process for the catalytic oxidation of an alkane to an unsaturated carboxylic acid or aldehyde is the identification of a catalyst having adequate conversion and suitable selectivity, thereby providing sufficient yield of the unsaturated carboxylic acid or aldehyde end-product. U.S. Pat. No. 5,380,933 discloses a method for preparing a catalyst useful in the gas phase oxidation of an alkane to an unsaturated carboxylic acid. In the disclosed method, a catalyst was prepared by combining ammonium metavanadate, telluric acid and ammonium paramolybdate to obtain a uniform aqueous solution. To this solution was added ammonium niobium oxalate to obtain a slurry. The water was removed from the slurry and a solid catalyst precursor resulted. The solid catalyst precursor was molded into a tablet, sieved to a desired particle size and then calcined at 600° C. under a nitrogen stream to obtain the desired catalyst. The resulting catalyst was asserted to be effective to convert propane to acrylic acid.

Co-pending U.S. patent application Ser. No. 09/316,007 discloses an improved process for preparing a catalyst useful in the conversion of propane to acrylic acid. The process was characterized by the use of a mixed mixed oxide solution which was stripped by various processes and calcined under an inert atmosphere.

The present inventors have now discovered a novel catalyst useful for catalyzing the oxidation of an alkane into an unsaturated aldehyde or carboxylic acid.

In one aspect of the present invention, there is provided a catalyst including: a mixed metal oxide of the formula $A_aM_mN_nX_xO_o$; and an acid selected from at least one of: (i) heteropolyacids, (ii) aluminas, (iii) zirconias, (iv) titanias, (v) zeolites, and (vi) acid combinations thereof, wherein $0.25<a<0.98$, $0.003<m<0.5$, $0.003<n<0.5$, $0.003<x<0.5$; the acid is present at from 0.05 to 5 weight percent based on the total weight of the catalyst; o is dependent on the oxidation state of the other elements; and A is selected from Mo, W, Fe, Nb, Ta, Zr, Ru, and mixtures thereof; M is selected from V, Ce, Cr, and mixtures thereof; N is selected from Te, Bi, Sb, Se, and mixtures thereof; and X is selected from Nb, Ta, W, Ti, Al, Zr, Cr, Mn, Fe, Ru, Co, Rh, Ni, Pd, Pt, Sb, Bi, B, In, Ce, and mixtures thereof.

In a second aspect of the present invention, there is provided a process for preparing a catalyst including: (A) admixing metal compounds, at least one of which is an oxygen containing compound, and water to form an aqueous solution; (B) removing the water from the aqueous solution to obtain a mixed metal oxide catalyst precursor; and (C) calcining the catalyst precursor at a temperature from 400° C. to 800° C. under an inert atmosphere; and (D) admixing an acid selected from at least one of: (i) heteropolyacids, (ii) aluminas, (iii) zirconias, (iv) titanias, (v) zeolites, and (vi) acid combinations thereof; to form a catalyst material including a mixed metal oxide having the formula $A_aM_mN_nX_xO_o$ and the acid, wherein $0.35<a<0.87$, $0.045<m<0.37$, $0.020<n<0.27$, $0.005<x<0.35$, the acid is present at from 0.05 to 5 weight percent based on the total weight of the catalyst, o is dependent on the oxidation state of the other elements, and A is selected from Mo, W, and mixtures thereof; M is selected from V, Ce, Cr, and mixtures thereof; N is selected from Te, Bi, Sb, and mixtures thereof; and X is selected from Nb, Ta, Zr, and mixtures thereof.

In a third aspect, the present invention includes a process for preparing a catalyst including: (A) admixing metal compounds, at least one of which is an oxygen containing compound, an acid selected from at least one of: (i) heteropolyacids, (ii) aluminas, (iii) zirconias, (iv) titanias, (v) zeolites, and (vi) acid combinations thereof; and water to form an aqueous solution; (B) removing the water from the aqueous solution to obtain a mixed metal oxide catalyst precursor; and (C) calcining the catalyst precursor at a temperature from 400° C. to 800° C. under an inert atmosphere to form a catalyst including a mixed metal oxide having the formula: $A_aM_mN_nX_xO_o$ and the acid, wherein $0.35<a<0.87$, $0.045<m<0.37$, $0.020<n<0.27$, $0.005<x<0.35$; the acid is present at from 0.05 to 5 weight percent based on the total weight of the catalyst; o is dependent on the oxidation state of the other elements, and A is selected from Mo, W, and mixtures thereof; M is selected from V, Ce, Cr, and mixtures thereof; N is selected from Te, Bi, Sb, and mixtures thereof; and X is selected from Nb, Ta, Zr, and mixtures thereof.

The present invention also provides a process for preparing a compound selected from the group consisting of an unsaturated aldehyde and a carboxylic acid including: subjecting an alkane to catalytic oxidation in the presence of the catalyst described above.

As used herein, the expression "(meth)acrylic acid" is intended to include both methacrylic acid and acrylic acid within its scope. In a like manner, the expression "(meth)acrylates" is intended to include both methacrylates and acrylates within its scope and the expression "(meth)acrolein" is intended to include both methacrolein and acrolein within its scope.

As used herein the terminology "($C_3$–$C_8$) alkane" means a straight chain or branched chain alkane having from 3 to 8 carbon atoms per alkane molecule.

As used herein the term "mixture" is meant to include within its scope all forms of mixtures including, but not limited to, simple mixtures as well as blends, alloys, etc.

For purposes of this application "% conversion" is equal to (moles of consumed alkane/moles of supplied alkane)× 100; "% selectivity" is equal to (moles of formed desired unsaturated carboxylic acid or aldehyde/moles of consumed alkane)×100; and "%yield" is equal to (moles of formed desired unsaturated carboxylic acid or aldehyde/moles of supplied alkane)×(carbon number of formed desired unsaturated carboxylic/acid or aldehydel carbon number of the supplied alkane)×100.

For purposes of this application by "solution" is meant that greater than 95 percent of metal solid added to a solvent is dissolved. It is to be understood that the greater the amount of metal solid not initially in solution, the poorer the performance of the catalyst derived therefrom will be.

For purposes of this application, by "catalyst material" is meant to include any form of catalyst, including, but not limited to powder, pellets, crystallized, supported catalysts and the like.

As recited above, a catalyst and processes for preparing a catalyst are disclosed. In a first step of the process a solution is formed by admixing metal compounds, at least one of which contains oxygen, and at least one solvent in appropriate amounts to form the solution. Generally, the metal compounds contain elements A, M, N, X, and O. In one embodiment, A is selected from Mo, W, Fe, Nb, Ta, Zr, Ru and mixtures thereof; M is selected from V, Ce, Cr and mixtures thereof; N is selected from Te, Bi, Sb, Se and mixtures thereof; and X is selected from Nb, Ta, W, Ti, Al, Zr, Cr, Mn, Fe, Ru, Co, Rh, Ni, Pd, Pt, Sb, Bi, B, In, Ce and mixtures thereof. In a preferred embodiment, A is selected from Mo, W and mixtures thereof; M is selected from V, Ce, Cr and mixtures thereof; N is selected from Te, Bi, Sb and mixtures thereof; and X is selected from Nb, Ta, Zr, and mixtures thereof In a more preferred embodiment, A is Mo, M is V, N is Te and X is Nb.

Suitable solvents include water, alcohols including, but not limited to, methanol, ethanol, propanol, diols, etc, as well as other polar solvents known in the art. Generally, water is preferred. The water is any water suitable for use in chemical synthesis including, without limitation, distilled water and de-ionized water. The amount of water present is that amount sufficient to keep the elements substantially in solution long enough to avoid or minimize compositional and/or phase segregation during the preparation steps. Accordingly, the amount of water will vary according to the amounts and solubility of materials combined. However, as stated above the amount of water must be sufficient to insure an aqueous solution is formed and not a slurry at the time of mixing.

Once the aqueous solution is formed, the water is removed by any suitable method known in the art to form a catalyst precursor. Such methods include, without limitation, vacuum drying, freeze drying, spray drying, rotary evaporation, and air drying. Vacuum drying is generally performed at pressures ranging from 10 to 500 mm/Hg. Freeze drying typically entails freezing the solution, using for instance liquid nitrogen, and drying the frozen solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and a pressure of from 10 mm/Hg to 760 mm/Hg, preferably at a bath temperature of from 40° C. to 90° C. and a pressure from 10 mm/Hg to 350 mm/Hg, more preferably from 40° C. to 60° C. and a pressure of from 10 mm/Hg to 40 mm/Hg. Air drying may occur at temperatures ranging from 25° C. to 90° C. Rotary evaporation or air drying are generally preferred.

Once obtained, the catalyst precursor is calcined under an inert atmosphere. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen, more preferably argon. The inert atmosphere may flow over the surface of the catalyst precursor or may not flow (a static environment). It is important to understand that by non-flow atmosphere is meant that the inert gas is not allowed to flow over the surface of the catalyst precursor. It is preferred that the inert atmosphere not flow over the surface of the catalyst precursor. However, when the inert atmosphere does flow over the surface of the catalyst precursor, the flow rate can vary over a wide range, for example, at a space velocity from 1 to 500 hr$^{-1}$.

The calcination is typically done at a temperature of from 350° C. to 850° C., preferably from 400° C. to 700° C., more preferably from 500° C. to 640° C. The calcination is typically performed for an amount of time suitable to form the catalyst. In one embodiment, the calcination is performed from 0.5 to 30 hours, preferably from 1 to 25 hours and more preferably from 1 to 15 hours.

With calcination, a mixed metal oxide is formed having the formula $$A_a M_m N_n X_x O_o$$

wherein A, M, N, and X are as described above. Molar ratios, a, m, n, and x are typically, from $0.25<a<0.98$, $0.003<m<0.5$, $0.003<n<0.5$, and $0.003<x<0.5$; preferably $0.35<a<0.87$, $0.045<m<0.37$, $0.020<n<0.27$, and $0.005<x<0.35$.

The molar ratio o, i.e., the amount of oxygen (O) present, is dependent on the oxidation state of the other elements in the catalyst. However, typically o is from 3 to 4.7, based on the other elements present in the mixed metal oxide.

In both processes of preparing the catalyst, an acid is admixed with the mixed metal oxide catalyst. In one embodiment of the invention, the acid is admixed with the metals and water, then the water is removed as described above to form the mixed metal oxide catalyst precursor, which is then calcined as described above to form the catalyst.

In another embodiment of the invention, the metals and water are admixed and the water is removed to form the mixed metal oxide catalyst precursor. The catalyst precursor is then calcined to form the catalyst. In this embodiment of the invention, the acid is then admixed with the catalyst. The admixture may be stirred, shaken, or ground by methods known in the art to ensure good mixing.

The acid utilized may be selected from at least one of heteropolyacids; aluminas, zirconias; titanias; zeolites or acid combinations thereof.

The heteropolyacids acids useful in this invention are cage-like structures with a primary, generally centrally located atom(s) surrounded by a cage framework, which framework contains a plurality of metal atoms, the same or different, bonded to oxygen atoms. The central element of heteropolyacids is different from metal atoms of the framework and is sometimes referred to as the "hetero" element or atom; the condensed coordination elements are referred to as the "framework" elements or metals, and are ordinarily transition metals. The majority of heteropolyacids have a centrally located heteroatom ("X") usually bonded in a tetrahedral fashion through four oxygen atoms to the "framework" metals ("M"). The framework metals, in turn, (i) are usually bonded to the central atom in an octahedral fashion through oxygens ("O"), and (ii) are bonded to four other framework metals through oxygen atoms and (iii) have a sixth non-bridging oxygen atom known as the "terminal oxygen" atom. This is illustrated by Formula (III).

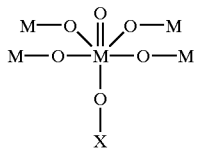
(III)

The principal framework metal, M, is any that has an appropriate cation radius and is a good oxygen pπ-electron acceptor. Typically, the framework metal is selected from molybdenum, tungsten, vanadium, niobium or tantalum. It is preferred that the framework metal is molybdenum, tungsten or vanadium.

Conventional heteropolyacids (and polyoxoanions thereof) can be described by the general formula $H_e(X_kM_nO_y)^{-e}$. In this formula, X, the central atom, is typically a Group 3–16 element, and preferably a Group 13–16 element. Suitable Group 13–16 elements include, but are not limited to: phosphorus, antimony, silicon and boron. It is preferred that the central atom, X, is phosphorus. The subscript "k" is typically from 1 to 5, and preferably 1 or 2. M is typically molybdenum, tungsten, or vanadium. The subscript "n" is typically from 5 to 20. The subscript "y" is typically from 18 to 62, and preferably about 40 to 62. The notation "e" is the negative charge on the $(X_kM_nO_y)$ polyoxoanion and will vary from case to case, but "e" is always the number of protons needed to balance the formula.

Heteropolyacids are known to exist in a variety of structures including the Keggin, Dawson and Anderson structures. These different structures correspond to the specific geometry of particular heteropolyacid compositions and vary according to the coordination chemistry and atomic radii of the metals present. Any of these structures, or mixtures thereof, are suitable for use in the present invention.

Framework-substituted heteropolyacids are also useful in the present invention. These compounds are heteropolyacids where certain framework atoms M (and the oxygen atoms doubly bonded to them) are replaced with transition metals. The substitution may, for example, be monosubstitution, random- or regio-disubstitution, random- or regio-trisubstitution, or higher substitutions, all of which produce effective compositions for use as supported heteropolyacid with a polyoxometallate support. Such polyoxymetallates are known in the art and are described for instance in U.S. Pat. No. 5,705,685 and U.S. patent application Ser. No. 09/002,816. Such patents being incorporated by reference to the extent of their teaching of polyoxymetallates. The catalysts may be further promoted by a variety of means described below. The present invention encompasses both unsubstituted and substituted heteropolyacids supported on salts of unsubstituted and substituted polyoxometallates.

A typical heteropolyacid useful in making the framework-substitute compositions has the formula $H_3PMo_{12}O_{40}$. When three Mo=O units are replaced with, e.g. iron (Fe), the resulting framework substituted heteropolyacid has the formula $H_6PMo_9Fe_3O_{37}$. Thus, the general formula of the regioselectively framework-substituted heteropolyacids described above becomes:

wherein k is from 1 to 5, n is from 5 to 19, m is from 1 to 6 and y is from 18 to 62. In this formula, $M^1$ comprises one or more of zinc or any of the transition metals, namely the Group 3–10 metals of the periodic table. Preferably the transition metal is an element selected from Groups 8–10 or the first row of Groups 4–7, such as, but not limited to: iron, cobalt, nickel, ruthenium, rhodium, palladium, osmium, iridium, platinum (Groups 8–10) or titanium, vanadium, chromium, manganese (Groups 4–7, first row). Among the more preferred $M^1$ metals are iron, manganese, vanadium and combinations of nickel and iron or other transition metal. The three $M^1$ atoms do not have to be the same. However, the three $M^1$ atoms must be different from the three M atoms replaced.

The heteropolyacids useful in the present invention are typically soluble in water and polar organic solvents such as acetonitrile and alcohols such as methanol. Such heteropolyacids are of the formula

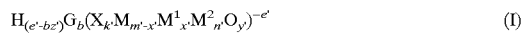
(I)

wherein G is an element selected from Groups 1–16 or an oxy ion thereof; X is an element selected from Groups 3–16; M=molybdenum, tungsten or a combination thereof; $M^1$=vanadium; $M^2$ is transition metal different from M and $M^1$; z'=the charge on G; b=0 to 12; k'=1 to 5; m'=5 to 20; x'=0 to 6; n'=0 to 3; y'=18 to 62; and e' is the charge of the polyoxometallate anion. Suitable elements for G include, but are not limited to: titanium, zirconium, hafnium, vanadium, niobium, tantalum, chromium, molybdenum, tungsten, manganese, rhenium, iron, cobalt, nickel, ruthenium, rhodium, palladium, osmium, iridium, platinum, copper, zinc, or combinations thereof. Suitable oxy anions of elements for G include, but are not limited to: titanyl, vanadyl, niobyl, or combinations thereof. Suitable transition elements for X include, but are not limited to: phosphorus, silicon, gallium, aluminum, arsenic, germanium, boron, cobalt, cerium, praseodymium, uranium, thorium or mixtures thereof. Suitable transition elements for $M^2$ include, but are not limited to: titanium, zirconium, hafnium, vanadium, niobium, tantalum, chromium, molybdenum, tungsten, manganese, rhenium, iron, cobalt, nickel, ruthenium, rhodium, palladium, osmium, iridium, platinum, copper, zinc or combinations thereof. It is preferred that when M is a combination of molybdenum and tungsten and the compound is a Keggin ion, x'=0. It is also preferred that when M is molybdenum and the compound is a Keggin ion, x'=0 to 3. It is further preferred that when M is tungsten and the compound is a Keggin ion, x'=0 to 6.

In the above formula (e'-bz') describes the number of protons ("$H^+$") present in the heteropolyacid component of the catalyst. At a minimum, (e'-bz') is preferably greater than or equal to 0.1. In one embodiment of the invention, (e'-bz') is greater than or equal to 0.5, in another it is greater than or equal to 1. In some embodiments, bz' equals zero and the number of protons in the heteropolyacids is e'. In another embodiment, (e'-bz') is formally 0 and the protons are added by treating the system with another acid, such as sulfuric acid.

Specific examples of heteropolyacids useful in the present invention include, but are not limited to: $H_3PMo_{12}O_{40}$, $H_3PW_{12}O_{40}$, $(VO)_{1.5}PMo_{12}O_{40}$, $(VO)_{1.5}PW_{12}O_{40}$, $(TiO)_{1.5}PMo_{12}O_{40}$, $H(VO)PMo_{12}O_{40}$, $H(VO)PW_{12}O_{40}$, $H_6PV_3Mo_9O_{40}$, $H_5PV_2Mo_{10}O_{40}$, $H_5PV_2W_{10}O_{40}$, $H_4PVMo_{11}O_{40}$, $H_4PVW_{11}O_{40}$, $RhPMo_{12}O_{40}$, $BiPMo_{12}O_{40}$, $HCrPVMo_{10}O_{40}$, $HBiPVMo_{10}O_{40}$, or combinations thereof. It is preferred that the heteropolyacid is $H_3PMo_{12}O_{40}$, $H_3PW_{12}O_{40}$, $(VO)_{1.5}PMo_{12}O_{40}$, $H(VO)PMo_{12}O_{40}$, $H_5PV_2Mo_{10}O_{40}$, $H_4PVMo_{11}O_{40}$, $RhPMo_{12}O_{40}$, $HCrPVMo_{11}O_{40}$, or $HBiPVMo_{11}O_{40}$. It is more preferred that the heteropolyacid is $H_3PMo_{12}O_{40}$ or $H_3PW_{12}O_{40}$. When the heteropolyacid is, for example, $(VO)_{1.5}PMo_{12}O_{40}$, $(TiO)_{1.5}PMo_{12}O_{40}$, $RhPMo_{12}O_{40}$, or $BiPMo_{12}O_{40}$, the necessar acid typically comes from a separate acid source, such as sulfuric acid in the $VOSO_4$ used to make $(VO)_{1.5}PMo_{12}O_{40}$. Such amount of acid is sufficient for the present invention.

The heteropolyacids useful in the present invention are commercially available or may be prepared by a variety of methods known in the art. General syntheses of the polyoxometallates and heteropolyacids useful in the present invention are described in Pope et. al., *Heteropoly and Isopoly Oxometallates,* Springer-Verlag, New York (1983). Typically, heteropolyacids are prepared by dissolving the desired metal oxides in water, adjusting the pH to approximately 1 to 2 with acid, such as hydrochloric acid, to provide the necessary protons, and then evaporating water until the desired heteropolyacid precipitates. As an example, the heteropolyacid $H_3PMo_{12}O_{40}$ can be prepared by combining $Na_2HPO_4$ and $Na_2MoO_4$, adjusting the pH with sulfuric acid, extracting with ether, and crystallizing the resulting heteropolyacid in water. Also, vanadium-substituted heteropolyacids may be prepared according to the method described in V. F. Odyakov, et. al., *Kinetics and Catalysis,* 1995, vol. 36, p. 733. The $Cs_3PMo_{12}O_{40}$ support can be prepared, as further described below, by treating the above heteropolyacid with cesium carbonate and collecting the resulting precipitated product.

The aluminas useful in the present invention may be any alumina suitable for use with mixed metal oxides to form a catalyst material and include, but are not limited to, γ-alumina and amorphous silica aluminas as well as acid mixtures thereof.

The zirconias useful in the present invention may be any zirconia suitable for use with mixed metal oxides to form a catalyst material and include, but are not limited to, sulfated zirconia, tungsten zirconia, molybdenum zirconia, and silica zirconias as well as acid mixtures thereof.

The titanias useful in the present invention may be any titania suitable for use with mixed metal oxides to form a catalyst material and include, but are not limited to anatase, rutile, and silica titanias as well as acid mixtures thereof.

The zeolites useful in the present invention may be any zeolite suitable for use with mixed metal oxides to form a catalyst material and include, but are not limited to Y, ZSM-5, and beta as well as acid mixtures thereof.

The amount of acid may range from 0.05 to 5 weight percent based on the total weight of the catalyst, preferably from 0.1 to 5 weight percent based on the total weight of the catalyst, more preferably from 0.5 to 5 weight percent based on the total weight of the catalyst.

The catalysts of the present invention are useful for manufacturing unsaturated aldehydes or a carboxylic acids from an alkane prepared by the process of the present invention. The catalyst may be prepared by any embodiment of the processes for making catalyst described herein. Furthermore, the catalyst may be used as a solid catalyst alone or may be utilized with a suitable support such as, without limitation, silica; diatomaceous earths (also known as clays), such as Kaolin or Thiele in layered and/or pillared forms; magnesium oxides and salts; and the like. The shape of the catalyst can be any suitable shape and will depend upon the particular application of the catalyst. In a like manner, the particle size of the catalyst may be any suitable particle size depending on the particular use of the catalyst.

Accordingly, a further aspect of the present invention is a process for preparing a compound selected from the group consisting of an unsaturated aldehyde and a carboxylic acid including subjecting an alkane to catalytic oxidation in the presence of a catalyst prepared according to the present invention.

The starting materials are generally an alkane gas or gases and an at least one oxygen containing gas. It is preferred that the starting materials also include steam. Accordingly, a starting material gas is supplied to the system which includes a gas mixture of at least one alkane and steam. The at least one oxygen-containing gas may be included in this mixture or be supplied separately. Furthermore, a diluting gas such as an inert gas including, without limitation, nitrogen, argon, helium, steam, or carbon dioxide may also be included. The diluting gas may be used to dilute the starting material and/or to adjust the space velocity, the oxygen partial pressure, and the steam partial pressure od the starting materials.

Suitable molar ratios of the alkane/oxygen/diluting gas/water in the starting material gas mixture are known in the art as well as the feed ratio of alkane/air/steam. For instance suitable ranges are disclosed in U.S. Pat. No. 5,380,933.

The starting material alkane is generally any alkane suitable for gas phase oxidation into an unsaturated aldehyde or carboxylic acid. Generally, the alkane is a $C_3$–$C_8$ alkane, preferably propane, isobutane or n-butane, more preferably propane or isobutane, most preferably propane. Furthermore, in another embodiment the alkane may be a mixture of alkanes including $C_3$–$C_8$ alkanes as well as lower alkanes such as methane and ethane.

The at least one oxygen-containing gas used may be pure oxygen gas, an oxygen containing gas such as air, an oxygen enriched gas, or a mixture thereof.

In a preferred embodiment, the starting material is a gas mixture of propane, air, and steam. The starting gas mixture is subjected to catalytic oxidation in the presence of the catalyst of the present invention. The catalyst may be in a fluidized bed or a fixed bed reactor. The reaction is generally conducted under atmospheric pressure, but may be conducted under elevated or reduced pressure. The reaction temperature is generally from 200° C. to 550° C., preferably 300° C. to 480° C., more preferably 350° C. to 440° C. The gas space velocity is generally 100 to 10,000 $hr^{-1}$, preferably 300 to 6,000 $hr^{-1}$, more preferably 300 to 3,000 $hr^{-1}$.

Also, in the method of the present invention it is to be understood that an unsaturated aldehyde may also be formed. For instance when propane is the starting alkane, acrolein may be formed and when isobutane is the starting alkane, methacrolein may be formed.

Abbreviations used throughout this application are:

| | | |
|---|---|---|
| ° C. = degrees Centigrade | mm = millimeters | Hg = Mercury |
| g = grams | cm = centimeters | mmole = millimoles |
| % = percent by weight | ml/min = milliliters per minute | |
| $N_2$ = nitrogen | wt % = weight percent | |

The following examples illustrate the process of the present invention. Based on the amount of starting material used, if there was no compositional segregation, or there was no loss of certain elements during the preparation steps, all of the mixed metal oxide samples prepared as follows should have an empirical formula of $Mo_1V_{0.3}Te_{0.23}Nb_{0.10-0.12}O_n$, unless otherwise indicated, where n is determined by the oxidation state of the other elements. The solutions or slurries containing the desired metal elements were prepared by heating the appropriate compounds in water at a temperature ranging from 25° C. to 95° C. When necessary, the solutions or slurries were cooled to temperatures ranging from 25° C. to 60° C. The water was then removed from the solutions or slurries by the appropriate drying method at pressures ranging from 760 mm/Hg to 10 mm/Hg.

EXAMPLE 1

This example describes the preparation of the hydrous zirconia used in Examples 2–4. $Zr(OH)_4$ was prepared by dissolving 300 g of $ZrOCl_2 \cdot 8H_2O$ in 4.5 L of deionized water. A 10 M $NH_4OH$ solution was added to a pH target of 9 to precipitate out the $Zr(OH)_4$. The precipitate was filtered, washed with water, and then dried overnight at 120° C. to provide dried $Zr(OH)_4$.

EXAMPLE 2

This example describes the preparation of sulfated zirconia ("SZ") solid acid. The dried $Zr(OH)_4$ (10 g) from Example 1 was impregnated by incipient wetness using either $H_2SO_4$ (0.9 g) or $(NH_4)_2SO_4$ (0.9 g). The impregnated zirconia was dried overnight in air and calcined in air at 700° C. for 3 hrs to provide SZ solid acid.

EXAMPLE 3

This example describes the preparation of tungsten zirconia ("W/Zr") solid acid. The dried $Zr(OH)_4$ (10 g) from Example 1 was impregnated by incipient wetness using ammonium metatungstate $[(NH_4)_6H_2W_{12}O_{40} \cdot nH_2O]$ (2.4 g) dissolved in 10 ml of water. The impregnated zirconia was dried overnight in air and calcined in air at 825° C. for 3 hrs to provide W/Zr solid acid.

EXAMPLE 4

This example describes the preparation of molybdenum zirconia ("Mo/Zr") solid acid. The dried $Zr(OH)_4$ (10 g) from Example 1 was impregnated by incipient wetness using an ammonium molybdate solution (3.6 g dissolved in 5 ml water). The impregnated zirconia was dried overnight in air and calcined in air at 825° C. for 3 hrs to provide Mo/Zr solid acid.

EXAMPLE 5

This describes the preparation of a mixed metal oxide. In a flask containing 420 g of water, 25.7 g of ammonium heptamolybdate tetrahydrate (Aldrich Chemical Company), 5.1 g of ammonium metavanadate (Aldrich Chemical Company) and 7.7 g of telluric acid (Aldrich Chemical Company) were dissolved upon heating to 80° C. After cooling to 39° C., 114.6 g of an aqueous solution of niobium oxalate (Reference Metals Company) containing 17.34 mmole of niobium was mixed to obtain a solution. The water of this solution was removed via a rotary evaporator with a warm water bath at 50° C. and 28 mm/Hg to obtain 44 g of precursor solid. Twenty g of the catalyst precursor solid was calcined in a covered crucible pre-purged with argon, non-flow environment at 600° C. for 2 hours, yielding a mixed metal oxide ("MMO") catalyst. The oven had previously been heated to 200° C. and held for one hour, then ramped to 600° C. During the calcination, the covered crucible was in a covered beaker with an Ar space velocity of 57 hr$^{-1}$. Because of the covered crucible, the argon did not flow over the precursor surface, but rather served to insure that the atmosphere outside the crucible remained argon. The atmosphere inside the crucible remained argon and off gasses from the catalyst.

EXAMPLE 6

The $SO_4/ZrO_2$ described in Example 2 was physically mixed with the mixed metal oxide from Example 5 in the following weight amounts: 0.0 wt %, 0.5 wt %, 1.0 wt %, 5.0 wt %, 10 wt %, and 100 wt %. The tungsten zirconia from EXAMPLE 3 was mixed with the mixed metal oxide from Example 5 as a 2.5 wt % mixture. The catalysts were tested for propane oxidation to acrylic acid under conditions of 380° C. and 2.5 seconds residence time using a 1 wt % propane, 3 wt % $H_2O$, 96 wt % air feed. Products were analyzed by FTIR. The results are shown in Table 1.

TABLE 1

| Catalyst | Acrylic Acid Yield (%) |
| --- | --- |
| 100% MMO | 7.8 |
| MMO + 0.5% SZ | 9.7 |
| MMO + 1% SZ | 8.1 |
| MMO + 5% SZ | 2.6 |
| MMO + 10% SZ | 0.9 |
| 100% SZ | 0.35 |
| MMO + 2.5% W/Zr | 9.9 |

The data indicate that there are yield advantages for catalysts containing lower levels of acid catalysts (~2.5 wt % acidic catalyst) over the mixed metal oxide base case. In addition, high levels of acid catalysts are deleterious with respect to yield. These results suggest an improved propane oxidation catalyst when an acidic component is combined physically with mixed metal oxide catalysts.

EXAMPLE 7

The molybdenum zirconia described in Example 4 was physically mixed with the mixed metal oxide from Example 5 in the following weight amounts: 0.0 wt %, 1.0 wt %, 5.0 wt %, 10 wt %, and 100 wt %. The catalysts were tested for propane oxidation to acrylic acid under the conditions described in Example 6. The results are shown in Table 2.

TABLE 2

| Catalyst | Acrylic Acid Yield (%) |
| --- | --- |
| 100% MMO | 9.6 |
| MMO + 1% Mo/Zr | 10.9 |
| MMO + 5% Mo/Zr | 9.6 |
| MMO + 10% Mo/Zr | 6.5 |
| 100% Mo/Zr | 0 |

The data indicate that at low levels of acid component in the catalyst (~1 wt %), yield benefits are seen. In addition, high levels of acid catalysts are deleterious with respect to yield. This result also suggests an improved propane oxidation catalyst when an acidic component is combined physically with mixed metal oxide catalysts.

EXAMPLE 8

Another batch of $Zr(OH)_4$ was prepared according to the process of Example 1. The material was calcined at 825° C.

for 3 hours in air. The calcined Zr(OH)$_4$ material (1 wt %) was admixed with the MMO material of Example 5 (99 wt %). The catalyst was then tested for propane oxidation to acrylic acid under the conditions described in Example 6. The results are shown in Table 3.

TABLE 3

| Catalyst | Acrylic Acid Yield (%) |
|---|---|
| 100% MMO | 14.1 |
| MMO + 1% Zr | 19.0 |

The data indicates that zirconium is a good acid catalyst to aid in the oxidation of propane to acrylic acid.

EXAMPLE 9

A sample containing a mixture of a mixed metal oxide catalyst and a heteropolyacid ("HPA") catalyst supported on a cesium polyoxometallate was prepared. The sample contained 0.14 g of $Mo_{1.00}V_{0.30}Te_{0.23}Nb_{0.08}O_x$ as the mixed metal oxide catalyst and 1 g of $Cs_3PMo_{12}O_{40}$ as the polyoxometallate support. $Cs_3PMo_{12}O_{40}$ was prepared by adding 33.31 g of $Cs_2CO_3$ in 1225 g deionized water to 159.47 g $H_3PMo_{12}O_{40}$ in 800 g deionized water at 50° C. The addition was performed over 2 hours and the mixture was maintained at 50° C. for an additional 30 minutes. After cooling to room temperature, the mixture was stirred slowly for approximately 70 hours. The water was then removed by evaporation and the resulting solid product was dried in a vacuum oven or at elevated temperature (for example 300° C.), yielding approximately 150 g of the desired polyoxometallate support.

Sample A was prepared by dry grinding the polyoxometallate with calcined mixed metal oxide followed by dry grinding with 20 mol % phosphomolybdic acid as the HPA. A second sample was prepared as described above, except the HPA was not included. Sample B was prepared by dry grinding the polyoxometallate with calcined mixed metal oxide.

Samples A–B were evaluated for their effectiveness in the conversion of propane to acrylic acid in a microreactor, under the conditions as described in Example 5. The results are reported in Table 4.

TABLE 4

| Sample | AA % Yield |
|---|---|
| A | 1.5 |
| B | 0.5 |

What is claimed:

1. A catalyst comprising:
   a mixed metal oxide of the formula $A_aM_mN_nX_xO_o$; and
   at least one acid selected from the group consisting of: (i) heteropolyacids, (ii) aluminas, (iii) zirconias, (iv) titanias, (v) zeolites, and (vi) acid combinations thereof;
   wherein $0.25<a<0.98$, $0.003<m<0.5$, $0.003<n<0.5$, $0.003<x<0.5$;
   the acid is present at from 0.05 to 5 weight percent based on the total weight of the catalyst;
   o is dependent on the oxidation state of the other elements; and
   A is selected from the group consisting of Mo, W, Nb, Ta, Zr, Ru, and mixtures thereof;
   M is selected from the group consisting of V, Ce, Cr, and mixtures thereof:
   N is selected from the group consisting of Te, Se, and mixtures thereof; and
   X is selected from the group consisting of Nb, Ta, W, Ti, Al, Zr, Cr, Mn, Ru, Co, Rh, Ni, Pd, Pt, Sb, B, In, Ce, and mixtures thereof.

2. The catalyst according to claim 1 wherein the catalyst comprises $0.35<a<0.87$, $0.045<m<0.37$, $0.020<n<0.27$, and $0.005<x<0.35$ and the acid is present at from 0.1 to 5 weight percent based on the total weight of the catalyst.

3. The catalyst according to claim 1, wherein; A is selected from the group consisting of Mo, W, and mixtures thereof; M is selected from the group consisting of V, Ce, Cr, and mixtures thereof; N is Te; X is selected from the group consisting of Nb, Ta, Zr, and mixtures thereof, and the acid is present at from 0.5 to 5 weight percent based on the total weight of the catalyst.

4. The catalyst according to claim 1, wherein A is Mo, M is V, N is Te, and X is Nb.

5. A process for preparing a catalyst comprising:
   (A) admixing metal compounds, at least one of which is an oxygen containing compound, and water to form an aqueous solution;
   (B) removing the water from the aqueous solution to obtain a mixed metal oxide catalyst precursor;
   (C) calcining the catalyst precursor at a temperature from 400° C. to 800° C. under an inert atmosphere; and
   (D) admixing at least one acid selected from the group consisting of:
      (i) heteropolyacids, (ii) aluminas, (iii) zirconias, (iv) titanias, (v) zeolites, and
      (vi) acid combinations thereof; to form a catalyst including a mixed metal oxide having the formula:

and the acid,
      wherein $0.35<a<0.87$, $0.045<m<0.37$, $0.020<n<0.27$, $0.005<x<0.35$;
      the acid is present at from 0.05 to 5 weight percent based on the total weight of the catalyst;
      o is dependent on the oxidation state of the other elements, and
      A is selected from the group consisting of Mo, W, and mixtures thereof;
      M is selected from the group consisting of V, Ce, Cr, and mixtures thereof;
      N is Te; and
      X is selected from the group consisting of Nb, Ta, Zr, and mixtures thereof.

6. The catalyst prepared according to the process of claim 5.

7. The catalyst according to claim 6, wherein the catalyst comprises $0.35<a<0.87$, $0.045<m<0.37$, $0.020<n<0.27$, and $0.005<x<0.35$ and the acid is present at from 0.1 to 5 weight percent based on the total weight of the catalyst.

8. The catalyst according to claim 6 wherein A is Mo, M is V, N is Te and X is Nb.

9. A process for preparing a catalyst comprising:
   (A) admixing metal compounds, at least one of which is an oxygen containing compound, at least one acid selected from the group consisting of: (i) heteropolyacids, (ii) aluminas, (iii) zirconias, (iv) titanias, (v) zeolites, and (vi) acid combinations thereof; and water to form an aqueous solution;

(B) removing the water from the aqueous solution to obtain a mixed metal oxide catalyst precursor; and (C) calcining the catalyst precursor at a temperature from 400° C. to 800° C. under an inert atmosphere to form a catalyst including a mixed metal oxide having the formula $$A_a M_m N_n X_x O_o$$

and the acid,
wherein $0.35<a<0.87$, $0.045<m<0.37$, $0.020<n<0.27$, $0.005<x<0.35$;

the acid is present at from 0.05 to 5 weight percent based on the total weight of the catalyst;

o is dependent on the oxidation state of the other elements, and

A is selected from the group consisting of Mo, W and mixtures thereof;

M is selected from the group consisting of V, Ce, Cr, and mixtures thereof;

N is Te; and

X is selected from the group consisting of Nb, Ta, Zr, and mixtures thereof.

* * * * *